(12) United States Patent
Huynh

(10) Patent No.: US 7,741,353 B2
(45) Date of Patent: *Jun. 22, 2010

(54) LEAD-FREE PRIMARY EXPLOSIVES

(75) Inventor: My Hang V. Huynh, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 363 days.

This patent is subject to a terminal disclaimer.

(21) Appl. No.: 11/803,839

(22) Filed: May 15, 2007

(65) Prior Publication Data

US 2008/0091029 A1 Apr. 17, 2008

Related U.S. Application Data

(60) Provisional application No. 60/800,678, filed on May 15, 2006.

(51) Int. Cl.
*C07D 257/04* (2006.01)
*A61K 31/41* (2006.01)

(52) U.S. Cl. .................. 514/381; 548/250
(58) Field of Classification Search .......... None
See application file for complete search history.

(56) References Cited

U.S. PATENT DOCUMENTS 6,123,790 A 9/2000 Lundstrom et al.
7,498,446 B2 * 3/2009 Hiskey et al. ............ 548/250

2006/0030715 A1 2/2006 Hiskey et al.

OTHER PUBLICATIONS

Huynh, et al. PNAS, 103(14), pp. 5409-5412 (2006), published online Mar. 27, 2006.*
My Hang V. Huynh et al, *Green primaries: Environmentally friendly energetic complexes*, Proc. Natl. Acad. Sci. USA 2006, 103(14), 5409-5412.
My Hang V. Huynh et al, *Synthesis, Characterization, and Energetic Properties of Diazido Heteroaromatic High-Nitrogen C—N Compound*, J. Am. Chem. Soc. 2005, 127, 12537-12543.
My Hang V. Huynh et al, *Green primary explosives: 5-Nitrotetrazolato-$N^2$-ferrate hierarchies*, Proc. Natl. Acad. Sci. USA 2006, 103(27), 10322-10327.
My Hang V. Huynh et al, *Formation and Reactivity of the Osmium (IV)—Cyanoimido Complex $[Os^{IV}(bpy)(Cl)_3(NCN)]$*, Angew. Chem. Int. Ed. 2001 Proc. Natl. Acad. Sci. USA, 40, No. 16, 3037-3039.
Gregory W. Drake et al, *Structural and Theoretical Investigations of 3,4,5-Triamino-1,2,4-Triazolium Salts*, Propellants Explos. Pyrotech. 30, No. 5, 329-337.
My Hang V. Huynh et al, Formation and O-Atom Reactivity of the Os(IV)—Sulfilimido and Os(IV)—Sulfoximido Complexes, cis-/trans-$[Os^{IV}(tpy)(Cl)_2(NSC_6H_3Me_2)]$ and cis-/trans-$[Os^{IV}(tpy)(Cl)_2(NS(O)C_6H_3Me_2)]$, J. Am. Chem. Soc. 2001, 123, 9170-9171.

* cited by examiner

*Primary Examiner*—Kamal A Saeed
*Assistant Examiner*—Michael Barker
(74) *Attorney, Agent, or Firm*—Bruce H. Cottrell; Holly L. Teeter; Samuel L. Borkowsky

(57) ABSTRACT

Lead-free primary explosives of the formula $(cat)_Y[M^{II}(T)_X(H_2O)_{6-X}]_Z$, where T is 5-nitrotetrazolate, and syntheses thereof are described. Substantially stoichiometric equivalents of the reactants lead to high yields of pure compositions thereby avoiding dangerous purification steps.

3 Claims, 2 Drawing Sheets

LEAD-FREE PRIMARY EXPLOSIVES

RELATED APPLICATIONS

This application claims the benefit of U.S. Provisional Application No. 60/800,678, filed May 15, 2006.

STATEMENT OF FEDERAL RIGHTS

The United States government has rights in this invention pursuant to Contract No. DE-AC52-06NA25396 between the United States Department of Energy and Los Alamos National Security, LLC for the operation of Los Alamos National Laboratory.

FIELD OF INVENTION

The present invention relates to lead-free primary explosives.

BACKGROUND

Primary explosives are used in small quantities to generate a detonation wave when subjected to a flame, heat, impact, electric spark, or friction. Detonation of the primary explosive initiates the secondary booster, main-charge explosive, or propellant.

Toxic mercury fulminate, lead azide, and lead styphnate are three common primary explosives, but their deleterious environmental impacts and effects on human health have made their replacement essential. Countless numbers of energetic compounds have been designed and screened as possible primaries, including organic compounds, organic salts, zwitterions, simple organic salts, coordination complexes, and metastable interstitial composites, but none have simultaneously met the six criteria for green primaries: (i) insensitive to moisture and light; (ii) sensitive to initiation but not too sensitive to handle and transport; (iii) thermally stable to at least 200° C.; (iv) chemically stable for extended periods; (v) devoid of toxic metals such as lead, mercury, silver, barium, or antimony; and (vi) free of perchlorate. Thus, a need remains for environmentally friendly, or green, primary explosives.

SUMMARY OF THE INVENTION

The present invention discloses novel lead-free compounds. More particularly, the present invention is directed to compounds of the formula $(cat)_Y[M^{II}(T)_X(H_2O)_{6-X}]_Z$ wherein cat is a cation independently selected from the group consisting of
  (a) alkali metals,
  (b) alkaline earth metals,
  (c) aliphatic and catenated high-nitrogen cations, and
  (d) heterocyclic nitrogen cations;
$M^{II}$ is a metal in the oxidation state plus-two independently selected from the group consisting of
  (a) cobalt,
  (b) copper,
  (c) iron,
  (d) manganese,
  (e) nickel, and
  (f) zinc;
T is the ligand 5-nitrotetrazolate ("NT"); and
X is an integer from 3 to 6;
Y is an integer from 1 to 4; and
Z is an integer from 1 to 2.

DETAILED DESCRIPTION

The present invention discloses novel lead-free compounds. More particularly, the present invention is directed to compounds of the formula $(cat)_Y[M^{II}(T)_X(H_2O)_{6-X}]_Z$ wherein
cat is a cation independently selected from the group consisting of
  (a) alkali metals,
  (b) alkaline earth metals,
  (c) aliphatic and catenated high-nitrogen cations, and
  (d) heterocyclic nitrogen cations;
$M^{II}$ is a metal in the oxidation state plus-two independently selected from the group consisting of
  (a) cobalt,
  (b) copper,
  (c) iron,
  (d) manganese,
  (e) nickel, and
  (f) zinc;
T is the ligand 5-nitrotetrazolate ("NT"); and
X is an integer from 3 to 6;
Y is an integer from 1 to 4; and
Z is an integer from 1 to 2.

Figure 1:
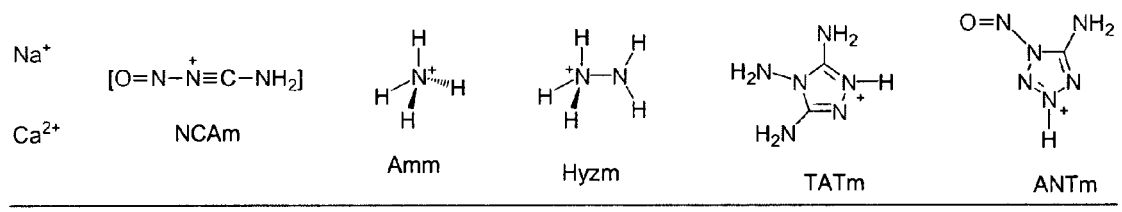
FIG. 1 shows representative cations.

The novel compounds may be prepared from numerous cations including alkali, alkaline earth, aliphatic and heterocyclic nitrogen compounds (see Huynh et al, *Proc. Natl. Acad. Sci. USA* 2006, 103(14), 5409-5412; Huynh et al, (2005) *J. Am. Chem. Soc.* 127, 12537-12543), and their catenated derivatives (see Huynh et al, *Proc. Natl. Acad. Sci. USA* 2006, 103(27), 10322-10327). Alkali metals comprise Group I of the periodic table and include lithium, sodium, potassium, rubidium, cesium, and francium. Alkaline earth metals comprise Group II of the periodic table and include beryllium, magnesium, calcium, strontium, barium, and radium. Aliphatic and catenated high-nitrogen cations include, but are not limited to, triaminoguanidinium ($TAG^+$), hydrazinium ($Hz^+$), nitrosocyanaminium (NCAm) (see Huynh et al, (2001) *Agnew. Chem. Int. Ed.* 40, 3037-3039), ammonium ($NH_4^+$), and hydrazonium (Hyzm) and others listed in Huynh et al (2005; cited above). Heterocyclic nitrogen cations include, but are not limited to, 3,3-dinitroazetidinium ($DNA^+$), 1,2,5-triamino-1,2,3-triazolium (TATm) (see Drake et al, (2005) *Propellants Explos. Pyrotech.* 30, 329-337), 5-amino-1-nitroso-1,2,3,4-tetrazolium (ANTm) (see Huynh et al, (2001) *J. Am. Chem. Soc.* 123, 9170-9171), 3,6-bis(guanidinium)-1,2,4,5-tetrazine ($BGTz^{2+}$), 3,6-bis(nitroguanidinium-1,2,4,5-tetrazine ($BNGTz^{2+}$), and 3,6-bis(hydrazinium)-1,2,4,5-tetrazine ($BHzTz^{2+}$). FIG. 1 shows representative cations.

The stability exhibited by transition metal primaries depends on the oxidation state of the metal, geometrical arrangement of ligands around the metal, and stereoelectronic (steric and electronic) effects of the ligands. Taking these factors into account, the novel compounds may be prepared from numerous transition metals with the oxidation state plus-two including, but not limited to, cobalt, copper, iron, manganese, nickel, and zinc.

Figure 2:
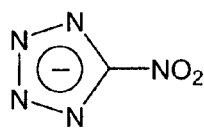
FIG. 2 shows 5-nitrotetrazolate.

The ligand must provide oxygen content and sensitivity to the metal complex anions. Therefore, the novel compounds may be prepared from oxygen-rich, sensitive, secondary high explosive anions. Mono- and di-substituted anions of tetrazole and di-substituted anions of triazole are favorable N-ligands for transition metals. Examples include, but are not limited to, 5-nitrotetrazolate ("NT") (shown in FIG. 2) and 1-amino-5-nitrotetrazole. Comparison of 1-amino-5 nitrotetrazole to 5-nitrotetrazolate reveals the latter to be the more energetic ligand because of its more positive oxygen balance ($OB_{CO}$) and higher energy content. Moreover, compared with all other heterocyclic five- and six-member rings, the 5-nitrotetrazolate has a much higher potential energy content because of the tetrazole backbone and the nitro group.

Figure 3:
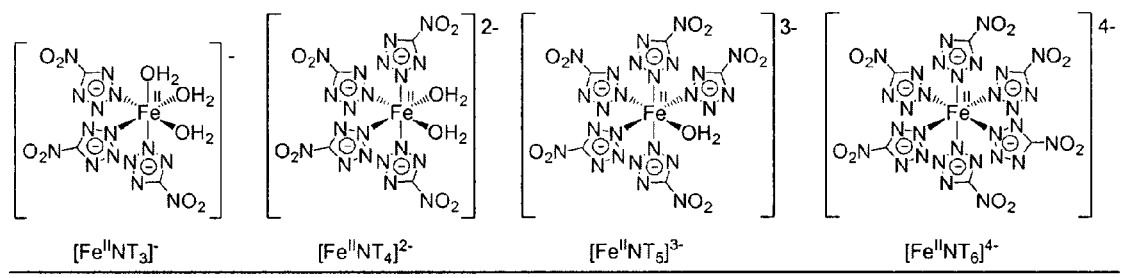
FIG. 3 shows 5-nitrotetrazolato-$N^2$-ferrate coordination complex anions.

Given six ligands around a metal center with the oxidation state of two-plus, four different coordinated anions can be assembled, namely $[M^{II}(T)_3(H_2O)_3]^-$, $[M^{II}(T)_4(H_2O)_2]^{2-}$, $[M^{II}(T)_5(H_2O)]^{3-}$, and $[M^{II}(T)_6]^{4-}$. FIG. 3 shows representative 5-Nitrotetrazolato-$N^2$-ferrate coordination complex anions. Each of these coordinated anions can be charge balanced by the cations listed above. For example, if the cation is calcium, then the above coordinated anions are charged balanced to produce the following compounds: $Ca[M^{II}(T)_3(H_2O)_3]_2$, $Ca[M^{II}(T)_4(H_2O)_2]$, $Ca_3[M^{II}(T)_5(H_2O)]_2$, and $Ca_2[M^{II}(T)_6]$.

In these coordination complex primaries, the coordination complex anions are the primary oxygen carrier as well as the sensitivity bearer whereas their cationic partners allow sensitivities (friction, impact, and flame) to be fine-tuned for various applications.

Because the $(cat)_Y[M^{II}(T)_X(H_2O)_{6-X}]_Z$ architecture satisfies all six criteria for green primaries, the compounds can be used as green primary explosives. The compounds are insensitive to spark even when dry. When wet by common organic solvents or water, they become insensitive to friction and impact and have no response to an open flame. This ease of desensitization makes them safe to prepare, store, handle, and transport. Before use, they are air-dried at room temperature. These compounds are sparingly soluble in most common organic solvents and water, structurally stable to light and moisture, and thermally stable to at least 200° C.

The novel compounds can be prepared by refluxing a chosen quantity of the metal salt and the desired salt of 5-nitrotetrazolate in a suitable solvent until the solution mixture becomes clear. Water is a suitable solvent for $[M^{II}(T)_3(H_2O)_3]^-$ and $[M^{II}(T)_4(H_2O)_2]^{2-}$, and absolute ethyl alcohol is a suitable solvent for $[M^{II}(T)_5(H_2O)]^{3-}$ and $[M^{II}(T)_6]^{4-}$. Upon cooling to room temperature with gentle stirring, the desired primary quantitatively precipitates leaving behind the colorless mother liquor. The product is filtered, washed thoroughly with fresh solvent, and air-dried.

Dangerous purification steps can be avoided by employing stoichiometric equivalents of the reactants to form a nearly quantitative single product. An excess quantity of any reactant might result in impurities.

Figure 4:
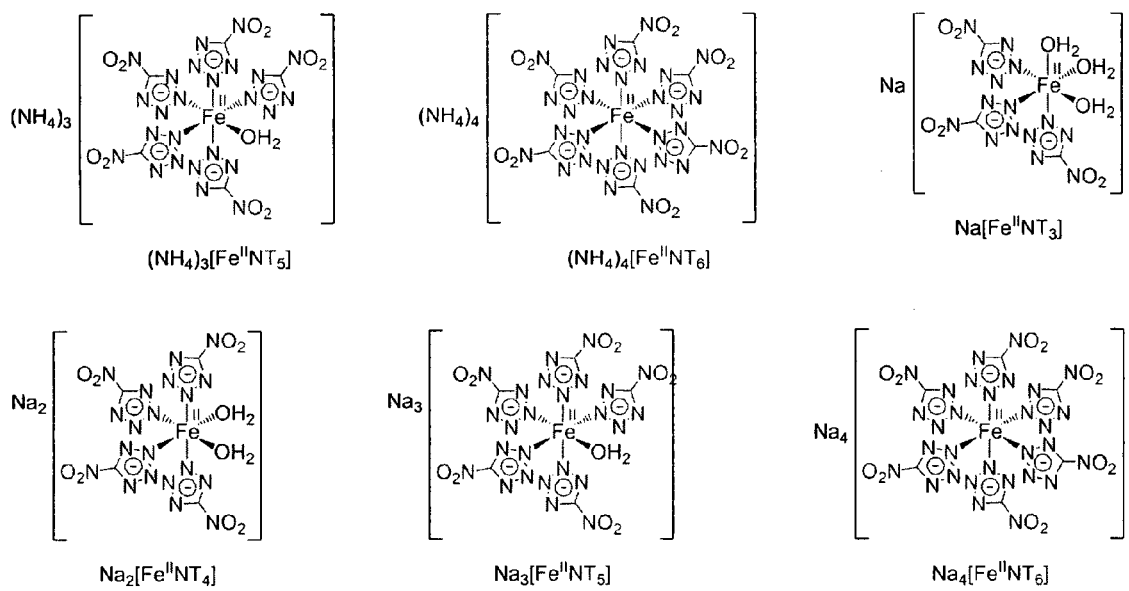
FIG. 4 shows six embodiments of the novel lead-free compounds.

Reference is now made in detail to various embodiments of the compounds. FIG. 4 shows possible configurations for six embodiments including $(NH_4)_3[Fe^{II}(NT)_5(H_2O)]$, $(NH_4)_4[Fe^{II}(NT)_6]$, $Na[Fe^{II}(NT)_3(H_2O)_3]$, $Na_2[Fe^{II}(NT)_4(H_2O)_2]$, $Na_3[Fe^{II}(NT)_5(H_2O)]$, and $Na_4[Fe^{II}(NT)_6]$.

Property measurements were taken for each compound. The density of the compound was determined using a solid pycnometry technique. The thermal decomposition temperature of the compound was determined using a Differential Scanning Calorimetry Exotherm performed with the rate of 5° C./minute.

Sensitivity measurements were taken for each compound. The impact sensitivity for the compound was measured by using a drop-weight machine type 12 test. Impact sensitivity is an average height in centimeters at which a 2.5 kilogram ("kg") is dropped onto a 40 milligram ("mg") sample of an explosive on 150-grit garnet sandpaper. The sample detonated if a sound level of 120 dB recorded from a microphone set 33 inches from the point of initiations. The test results are summarized as the height in centimeters ("cm") at which the probability of explosion is 50%.

Friction sensitivity was determined by mini BAM (with capability of measuring from 0 to 1000 grams ("g")) and BAM (with capability of measuring from 0.5 to 36 kg machines (Reichel & Partner, Rheinazbern, Germany). In each test, a rounded porcelain striker ground to set off 1 mg of explosive on a porcelain plate that is mechanically driven directly underneath the striker at a given weight. The striker was pivotal to a calibrated arm on which different weights can be hung. The criterion for detonation was an audible or visual reaction, or both, recognized by an operator. The test results are statistically reported as a 50% load with the explosive probability of 50%.

Spark sensitivity from 0 to 6 joules ("J") was measured by an ABL electrostatic discharge apparatus (Safety Management Services, West Jordan, Utah) connected to a diagnostic analyzer to detect $NO_X$, CO (0 to 5,000 parts per million ("ppm")), and $CO_2$ (0 to 1,000 ppm) released from a detonated sample. In an insulating plastic disk sat on a conductive steel base, a 2-to-3 mg sample was covered with a piece of Scotch Tape™ (3M Co.), and the assembly was centralized beneath a brass needle that would be charged when the instrument was initiated. This charged needle pierced through the Scotch Tape™, discharging the spark to set off the sample. The spark energy of the explosive sample was sent to the analyzer and recorded in joules.

EXAMPLE 1

Preparation of $(NH_4)[Fe^{II}(NT)_3(H_2O)_3]$

An iron compound was prepared in accordance with the reaction $[Fe(H_2O)_6](ClO_4)_2+3NH_4NT \rightarrow NH_4[Fe(NT)_3(H_2O)_3]+2NH_4ClO_4$ or $FeCl_2.4H_2O+3NH_4NT \rightarrow NH_4[Fe(NT)_3(H_2O)_3]+2NH_4Cl$ by mixing a solution of 1.00 g (7.57 millimol ("mmol") of ammonium 5-nitrotetrazolate in 30 milliliters ("mL") of water. The solution was slowly added to a 30 mL solution of 0.916 g (2.52 mmol) of $[Fe(H_2O)_6](ClO_4)_2$ or 0.502 g (2.52 mmol) of $FeCl_2.4H_2O$ with stirring. The orange and opaque solution was slowly brought to reflux for 2 hours. The clear orange solution was then slowly cooled to 10° C. at the rate of 3° C./minute and maintained at this temperature until the solution became colorless. Most of the mother liquor was decanted; the crystals were filtered, washed thoroughly with cold water, and air-dried.

Elemental analysis of the crystals, as set forth in TABLE 1, showed the composition corresponds to $(NH_4)[Fe^{II}(NT)_3(H_2O)_3]$.

TABLE 1

| $(NH_4)[Fe^{II}(NT)_3(H_2O)_3]$ | | | | |
|---|---|---|---|---|
| | CARBON (%) | HYDROGEN (%) | NITROGEN (%) | OXYGEN (%) |
| THEORETICAL | 7.67 | 2.14 | 47.68 | 30.63 |
| OBSERVED | 7.82 | 2.08 | 45.20 | 30.45 |

The above-described synthesis yielded 95% $(NH_4)[Fe^{II}(NT)_3(H_2O)_3]$.

The preparation procedure for $(NH_4)_2[Fe^{II}(NT)_4(H_2O)_2]$ is similar to that of $(NH_4)[Fe^{II}(NT)_3(H_2O)_3]$ except that the stoichiometric amount of the desired salt of 5-nitrotetrazolate was used. Elemental analysis of the crystals, as set forth in TABLE 2, showed the composition corresponds to $(NH_4)_2[Fe^{II}(NT)_4(H_2O)_2]$.

TABLE 2

$(NH_4)_2[Fe^{II}(NT)_4(H_2O)_2]$

| | CARBON (%) | HYDROGEN (%) | NITROGEN (%) | OXYGEN (%) |
|---|---|---|---|---|
| THEORETICAL | 8.22 | 2.07 | 52.75 | 27.39 |
| OBSERVED | 8.29 | 1.79 | 48.96 | 27.62 |

The above-described synthesis yielded 96% $(NH_4)_2[Fe^{II}(NT)_4(H_2O)_2]$.

The preparation procedures for $(NH_4)_3[Fe^{II}(NT)_5(H_2O)]$ and $(NH_4)_4[Fe^{II}(NT)_6]$ are similar to that of $(NH_4)[Fe^{II}(NT)_3(H_2O)_3]$ except that absolute ethyl alcohol was the solvent and the stoichiometric amount of the desired salt of 5-nitrotetrazolate was used. Elemental analysis of the crystals, as set forth in TABLES 3 and 4, showed the compositions correspond to $(NH_4)_3[Fe^{II}(NT)_5(H_2O)]$ and $(NH_4)_4[Fe^{II}(NT)_6]$, respectively.

TABLE 3

$(NH_4)_3[Fe^{II}(NT)_5(H_2O)]$

| | CARBON (%) | HYDROGEN (%) | NITROGEN (%) | OXYGEN (%) |
|---|---|---|---|---|
| THEORETICAL | 8.60 | 2.02 | 56.17 | 25.21 |
| OBSERVED | 8.71 | 1.96 | 55.12 | 25.49 |

The above-described synthesis yielded 92% $(NH_4)_3[Fe^{II}(NT)_5(H_2O)]$.

TABLE 4

$(NH_4)_4[Fe^{II}(NT)_6]$

| | CARBON (%) | HYDROGEN (%) | NITROGEN (%) | OXYGEN (%) |
|---|---|---|---|---|
| THEORETICAL | 8.87 | 1.99 | 58.63 | 23.64 |
| OBSERVED | 8.96 | 1.89 | 56.42 | 23.51 |

The above-described synthesis yielded 94% $(NH_4)_4[Fe^{II}(NT)_6]$.

Selected properties and sensitivities of ammonium 5-nitrotetrazolato-$N^2$-ferrate hierarchies are set forth in TABLE 5.

EXAMPLE 2

Preparation of $Na[Fe^{II}(NT)_3(H_2O)_3]$

An iron compound was prepared in accordance with the reaction $[Fe(H_2O)_6](ClO_4)_2+3NaNT.2H_2O \rightarrow Na[Fe(NT)_3(H_2O)_3]+2NaClO_4$ or $FeCl_2.4H_2O+3NaNT.2H_2O \rightarrow Na[Fe^{II}(NT)_3(H_2O)_3]+2NaCl$ by mixing a solution of 1.00 g (5.78 mmol) of sodium 5-nitrotetrazolate dihydrate in 20 mL of water. The solution was slowly added to a 30 mL solution of 0.699 g (1.93 mmol) of $[Fe(H_2O)_6](ClO_4)_2$ or 0.383 g (1.93 mmol) of $FeCl_2.4H_2O$ with stirring. The orange suspension was slowly brought to reflux for two hours. The clear solution was then slowly cooled to 10° C. at the rate of 3° C./minute and maintained at this temperature until the solution became colorless. Most of the mother liquor was decanted; the crystals were filtered, washed thoroughly with cold water, and air-dried.

Elemental analysis of the crystals, as set forth in TABLE 6, showed the composition corresponds to $Na[Fe^{II}(NT)_3(H_2O)_3]$.

TABLE 6

$Na[Fe^{II}(NT)_3(H_2O)_3]$

| | CARBON (%) | HYDROGEN (%) | NITROGEN (%) | OXYGEN (%) |
|---|---|---|---|---|
| THEORETICAL | 7.59 | 1.27 | 44.23 | 30.31 |
| OBSERVED | 7.72 | 1.34 | 42.86 | 30.66 |

The above-described synthesis yielded 94% $Na[Fe^{II}(NT)_3(H_2O)_3]$.

The preparation procedure for $Na_2[Fe^{II}(NT)_4(H_2O)_2]$ is similar to that of $Na[Fe^{II}(NT)_3(H_2O)_3]$ except that the stoichiometric amount of the desired salt of 5-nitrotetrazolate was used. Elemental analysis of the crystals, as set forth in TABLE 7, showed the composition corresponds to $Na_2[Fe^{II}(NT)_4(H_2O)_2]$.

TABLE 7

$Na_2[Fe^{II}(NT)_4(H_2O)_2]$

| | CARBON (%) | HYDROGEN (%) | NITROGEN (%) |
|---|---|---|---|
| THEORETICAL | 8.09 | 0.68 | 47.16 |
| OBSERVED | 8.22 | 0.74 | 46.97 |

The above-described synthesis yielded 92% $Na_2[Fe^{II}(NT)_4(H_2O)_2]$.

The preparation procedures for $Na_3[Fe^{II}(NT)_5(H_2O)]$ and $Na_4[Fe^{II}(NT)_6]$ are similar to that of $Na[Fe^{II}(NT)_3(H_2O)_3]$ except that absolute ethyl alcohol was the solvent and the stoichiometric amount of the desired salt of 5-nitrotetrazolate was used. Selected properties and sensitivities of sodium 5-nitrotetrazolato-$N^2$-ferrate hierarchies are set forth in TABLE 8.

TABLE 5

| | $(NH_4)[Fe^{II}(NT)_3(H_2O)_3]$ | $(NH_4)_2[Fe^{II}(NT)_4(H_2O)_2]$ | $(NH_4)_3[Fe^{II}(NT)_5(H_2O)]$ | $(NH_4)_4[Fe^{II}(NT)_6]$ |
|---|---|---|---|---|
| DENSITY, g/cm³ | 2.10 ± 0.02 | 2.20 ± 0.03 | 2.34 ± 0.02 | 2.45 ± 0.02 |
| THERMAL DECOMPOSITION TEMPERATURE, ° C. | 261 | 255 | 253 | 252 |
| SPARK, J | >0.36 | >0.36 | >0.36 | >0.36 |
| FRICTION, kg | 4.2 | 2.8 | 1.3 | 0.8 |
| IMPACT, cm | 15 | 12 | 10 | 8 |

TABLE 8

|  | $Na[Fe^{II}(NT)_3(H_2O)_3]$ | $Na_2[Fe^{II}(NT)_4(H_2O)_2]$ | $Na_3[Fe^{II}(NT)_5(H_2O)]$ | $Na_4[Fe^{II}(NT)_6]$ |
|---|---|---|---|---|
| DENSITY, g/cm$^3$ | 2.15 ± 0.03 | 2.25 ± 0.03 | 2.38 ± 0.03 | 2.47 ± 0.03 |
| THERMAL DECOMPOSITION TEMPERATURE, ° C. | 255 | 250 | 252 | 250 |
| SPARK, J | >0.36 | >0.36 | >0.36 | >0.36 |
| FRICTION, g | 36 | 20 | 17 | 12 |
| IMPACT, cm | 14 | 12 | 8 | 6 |

The preparation procedure for $Na[Cu^{II}(NT)_3(H_2O)_3]$, $Na_2[Cu^{II}(NT)_4(H_2O)_2]$, $Na_3[Cu^{II}(NT)_5(H_2O)]$, and $Na_4[Cu^{II}(NT)_6]$ are similar to those of $Na[Fe^{II}(NT)_3(H_2O)_3]$, $Na_2[Fe^{II}(NT)_4(H_2O)_2]$, $Na_3[Fe^{II}(NT)_5(H_2O)]$, and $Na_4[Fe^{II}(NT)_6]$, respectively, except that the stoichiometric amount of the copper metal hydrate salt was used. Similarly, the preparation procedure for $(NH_4)[Cu^{II}(NT)_3(H_2O)_3]$, $(NH_4)_2[Cu^{II}(NT)_4(H_2O)_2]$, $(NH_4)_3[Cu^{II}(NT)_5(H_2O)]$, and $(NH_4)_4[Cu^{II}(NT)_6]$ are similar to those of $(NH_4)[Fe^{II}(NT)_3(H_2O)_3]$, $(NH_4)_2[Fe^{II}(NT)_4(H_2O)_2]$, $(NH_4)_3[Fe^{II}(NT)_5(H_2O)]$, and $(NH_4)_4[Fe^{II}(NT)_6]$, respectively, except that the stoichiometric amount of the copper metal hydrate salt was used. Selected elemental analysis of crystals from the above procedures, as set forth in TABLES 9 and 10, showed the compositions correspond to $Na_2[Cu^{II}(NT)_4(H_2O)_2]$ and $(NH_4)_2[Cu^{II}(NT)_4(H_2O)_2]$, respectively.

TABLE 9

| | $Na_2[Cu^{II}(NT)_4(H_2O)_2]$ | | |
|---|---|---|---|
| | CARBON (%) | HYDROGEN (%) | NITROGEN (%) |
| THEORETICAL | 7.98 | 0.67 | 46.56 |
| OBSERVED | 8.02 | 0.72 | 46.55 |

The above-described synthesis yielded 94% $Na_2[Cu^{II}(NT)_4(H_2O)_2]$.

TABLE 10

| | $(NH_4)_2[Cu^{II}(NT)_4(H_2O)_2]$ | | | |
|---|---|---|---|---|
| | CARBON (%) | HYDROGEN (%) | NITROGEN (%) | OXYGEN (%) |
| THEORETICAL | 8.12 | 2.04 | 52.07 | 27.03 |
| OBSERVED | 8.06 | 1.80 | 48.65 | 27.73 |

The above-described synthesis yielded 93% $(NH_4)_2[Cu^{II}(NT)_4(H_2O)_2]$.

Selected properties and sensitivities of sodium and ammonia 5-nitrotetrazolato-N$^2$ ferrate and cupric are set forth in TABLE 11.

TABLE 11

|  | $(NH_4)_2[Fe^{II}(NT)_4(H_2O)_2]$ | $Na_2[Fe^{II}(NT)_4(H_2O)_2]$ | $(NH_4)_2[Cu^{II}(NT)_4(H_2O)_2]$ | $Na_2[Cu^{II}(NT)_4(H_2O)_2]$ |
|---|---|---|---|---|
| DENSITY, g/cm$^3$ | 2.20 ± 0.03 | 2.25 ± 0.03 | 2.06 ± 0.03 | 2.14 ± 0.02 |
| THERMAL DECOMPOSITION TEMPERATURE, ° C. | 255 | 250 | 265 | 259 |
| SPARK, J | >0.36 | >0.36 | >0.36 | >0.36 |
| FRICTION, g | 2,800 | 20 | 500 | 40 |
| IMPACT, cm | 12 | 12 | 12 | 12 |

It is understood that the foregoing detailed description and examples are merely illustrative and are not to be taken as limitations upon the scope of the invention, which is defined by the appended claims. Various changes and modifications to the disclosed embodiments will be apparent to those skilled in the art. Such changes and modifications, including without limitation those relating to chemical structures, syntheses, formulations and/or methods of use of the invention, may be made without departing from the spirit and scope thereof.

All publications, patents, and patent applications cited in this specification are herein incorporated by reference as if each individual publication or patent application were specifically and individually indicated to be incorporated by reference.

I claim:

1. A compound of formula $(cat)_Y[M^{II}(T)_X(H_2O)_{6-X}]_Z$ wherein cat is a cation independently selected from the group consisting of
   (a) alkali metals,
   (b) alkaline earth metals,
   (c) aliphatic and catenated high-nitrogen cations, and
   (d) heterocyclic nitrogen cations; and $M^{II}$ is a metal in the oxidation state plus-two independently selected from the group consisting of
   (a) cobalt,
   (b) copper,
   (c) iron,
   (d) manganese,
   (e) nickel, and
   (f) zinc;

T is the ligand 5-nitrotetrazolate ("NT"); and
   X is 6;
   Y is an integer from 1 to 4; and
   Z is an integer from 1 to 2.

2. A compound of the formula selected from the group consisting of $(NH_4)[Fe^{II}(NT)_3(H_2O)_3]$, $(NH_4)_3[Fe^{II}(NT)_5(H_2O)]$, $(NH_4)_4[Fe^{II}(NT)_6]$, $Na[Fe^{II}(NT)_3(H_2O)_3]$, $Na_3[Fe^{II}(NT)_5(H_2O)]$, and $Na_4[Fe^{II}(NT)_6]$.

3. A compound of the formula selected from the group consisting of $Na_3[Cu^{II}(NT)_5(H_2O)]$, $Na[Cu^{II}(NT)_3(H_2O)_3]$, $Na_4[Cu^{II}(NT)_6]$, $(NH_4)_3[Cu^{II}(NT)_5(H_2O)]$, and $(NH_4)_4[Cu^{II}(NT)_6]$.

* * * * *